US012599135B2

(12) United States Patent
Søndergaard et al.

(10) Patent No.: US 12,599,135 B2

(45) Date of Patent: Apr. 14, 2026

(54) COMPOSITION AND METHOD FOR PREPARING N-PHENYLPYRAZOLE-1-CARBOXAMIDES

(71) Applicants: FMC Corporation, Philadelphia, PA (US); FMC Agro Singapore Pte. Ltd., Singapore (SG)

(72) Inventors: Kåre Søndergaard, Holstebro (DK); Jack K. Vinther, Holstebro (DK)

(73) Assignee: FMC CORPORATION FMC IP TECHNOLOGY GMBH (CH)

( * ) Notice: Subject to any disclaimer, the term of this patent is extended or adjusted under 35 U.S.C. 154(b) by 467 days.

(21) Appl. No.: 18/017,275

(22) PCT Filed: Jul. 22, 2021

(86) PCT No.: PCT/US2021/042695
§ 371 (c)(1),
(2) Date: Jan. 20, 2023

(87) PCT Pub. No.: WO2022/020547
PCT Pub. Date: Jan. 27, 2022

(65) Prior Publication Data

US 2023/0263162 A1 Aug. 24, 2023

Related U.S. Application Data

(60) Provisional application No. 63/144,115, filed on Feb. 1, 2021, provisional application No. 63/055,443, filed on Jul. 23, 2020.

(51) Int. Cl.
*C07D 401/04* (2006.01)
*A01N 25/02* (2006.01)
*A01N 43/56* (2006.01)

(52) U.S. Cl.
CPC ............. *A01N 43/56* (2013.01); *A01N 25/02* (2013.01); *C07D 401/04* (2013.01)

(58) Field of Classification Search
CPC ....... A01N 43/56; A01N 25/02; C07D 401/04
See application file for complete search history.

(56) References Cited

U.S. PATENT DOCUMENTS

2006/0223816 A1 10/2006 Adin et al.

FOREIGN PATENT DOCUMENTS

WO 2011/006896 A2 1/2011
WO 2020/117493 * 6/2020

(Continued)

OTHER PUBLICATIONS

Parambil, et al., "Engineering Crystallography: From Molecule to Crystal to Functional Form", In: "Chapter 13: Seeding in Crystallisation", Springer, Jan. 1, 2017, p. 235-245.

(Continued)

*Primary Examiner* — D Margaret M Seaman
(74) *Attorney, Agent, or Firm* — FMC Corporation; D. Andrew Travis

(57) ABSTRACT

An improved method is disclosed for preparing an organic pesticide of Formula 4-A from (1) a composition comprising: (a) a crystalline organic pesticide; (b and c) compounds of Formulae 1 and 2; (d) an amine base and (e) an aprotic solvent; (2) reacting with a sulfonyl chloride of Formula 3; and (3) allowing the mixture to proceed to an organic pesticide of Formula 4-A.

Crystalline Organic Pesticide +

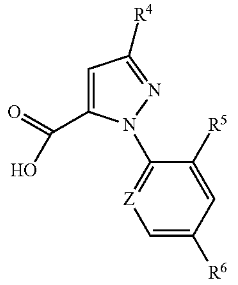

+

1

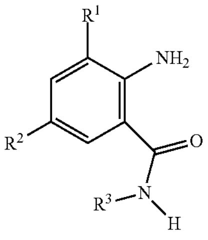

2

+ Amine Base + Aprotic Solvent $R^3S(O)_2Cl$
3

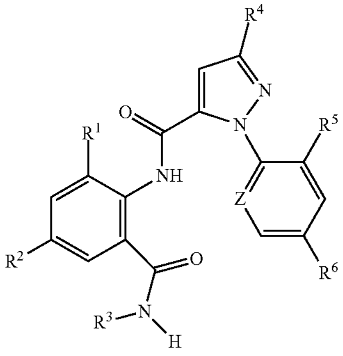

4-A wherein $R^1$, $R^2$, $R^3$, $R^4$, $R^5$, $R^6$, $R^7$ and $R^8$ are as defined in the disclosure.

11 Claims, No Drawings

(56) References Cited

FOREIGN PATENT DOCUMENTS

| | | | | | |
|---|---|---|---|---|---|
| WO | WO-2020117493 | A1 | * | 6/2020 | ........... C07D 231/14 |
| WO | 2021/188653 | A1 | | 9/2021 | |

OTHER PUBLICATIONS

International Search Report of Corresponding PCT/US2021/042695 patent application.

* cited by examiner

COMPOSITION AND METHOD FOR PREPARING N-PHENYLPYRAZOLE-1-CARBOXAMIDES

CROSS-REFERENCE TO RELATED APPLICATIONS

This application claims the benefit of U.S. Provisional Application Nos. 63/055,443, filed Jul. 23, 2020, and 63/144,115, filed Feb. 1, 2021, all of which are incorporated by reference herein in their entirety.

FIELD

This disclosure relates to a novel composition and improved method for preparing N-phenylpyrazole-1-carboxamides.

BACKGROUND

Conventional processes for the production of anthranilic diamides are subject to several industrial concerns, such as processability, environmental hazards, high cost, reagent reactivity, necessary specialized equipment, and limitations to operate the method on a commercial scale. New methods of producing high purity anthranilamides at higher commercial scales are needed.

The present disclosure provides novel methods useful for preparing cyantraniliprole, chlorantraniliprole and derivatives thereof. The benefits of the methods of the present disclosure compared to previous methods include a significant improvement in operating the process on a commercial scale by eliminating formation of viscous reaction mixture and the need for time-consuming cleaning of the reactor from batch to batch.

SUMMARY

In one aspect, the present disclosure provided herein is directed to a composition comprising:

(a) a crystalline organic pesticide, (b) a carboxylic acid compound of Formula 1,

1

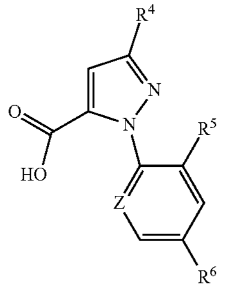

wherein $R^4$ is Cl, Br, $CF_3$, $OCF_2H$ or $OCH_2CF_3$;

$R^5$ is F, Cl or Br;

$R^6$ is H, F or Cl;

Z is $CR^7$ or N; and $R^7$ is H, F, Cl or Br;

(c) an aniline compound of Formula 2,

2

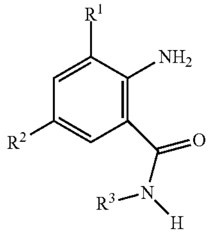

wherein $R^1$ is $CH_3$ or Cl;

$R^2$ is Br, Cl, I or CN;

$R^3$ is H or $C_1$-$C_4$ alkyl;

(d) an amine base and (e) an aprotic solvent.

In another aspect, the present disclosure provides a method to prepare a compound of Formula 4-A,

4-A

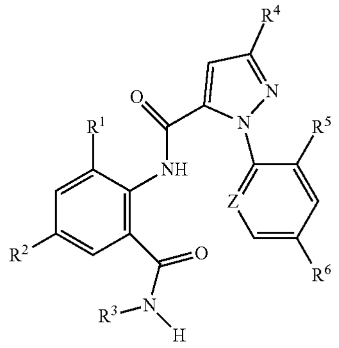

wherein $R^1$ is $CH_3$ or Cl;

$R^2$ is Br, Cl, I or CN;

$R^3$ is H or $C_1$-$C_4$ alkyl;

$R^4$ is Cl, Br, $CF_3$, $OCF_2H$ or $OCH_2CF_3$;

$R^5$ is F, Cl or Br;

$R^6$ is H, F or Cl;

Z is $CR^7$ or N; and $R^7$ is H, F, Cl or Br the method comprising the steps of:

(1) forming the composition, as set forth above;

(2) reacting the composition with a sulfonyl chloride compound of Formula 3, $R^8S(O)_2Cl$ 3 wherein $R^8$ is carbon-based radical; and (3) allowing the coupling of the acid activated mixture to proceed for the formation of a compound of Formula 4-A.

In another aspect, the present disclosure provides an organic pesticide of Formula 4-A formed using the composition, as set forth above.

DETAILED DESCRIPTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step, or ingredient not specified. If in the claim, such would close the claim to the inclusion of materials other than those expressly recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition, process or method that includes materials, steps, features, components, or elements, in addition to those literally disclosed, provided that these additional materials, steps, features, components, or elements do not materially affect the basic and novel characteristic(s) of the disclosure. The term "consisting essentially of" occupies a middle ground between "comprising" and "consisting of".

Where applicants have defined an embodiment or a portion thereof with an open-ended term such as "comprising," it should be readily understood that (unless otherwise stated) the description should be interpreted to also describe such an embodiment using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the disclosure are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As used herein, "amine base" refers to organic bases and salts thereof including primary, secondary and tertiary amines. Suitable amine bases include, but are not limited to, substituted amines, cyclic amines, naturally-occurring amines, such as pyridine bases (e.g., 3-picoline), N,N'-dibenzylethylenediamine, diethylamine, 2-diethylaminoethanol, 2-dimethylamino-ethanol, ethanolamine, ethylenediamine, N-ethylmorpholine, N-ethylpiperidine, isopropyl-amine, morpholine, piperazine, piperidine, triethylamine, trimethylamine, tripropylamine, tromethamine, and the like.

As used herein, "aprotic solvent" refers to any solvent not having a proton-donating ability. Examples include, without any limitation, acetonitrile, 2-methyltetrahydrofuran, tetrahydrofuran, ethyl acetate, propyl acetate (e.g., isopropyl acetate), acetone, dimethylsulfoxide, N,N-dimethylformamide, N,N-dimethylacetamide, N-methylpyrrolidone, hexamethylphosphoramide, and propylene carbonate.

As used herein, the term "polar aprotic solvent" refers to an aprotic solvent that is a polar solvent. Examples include, without any limitation, acetonitrile, N,N-dimethylformamide, and the like.

As used herein, the term "acid activating agent" refers to a reactant that facilitates coupling of a carboxylic acid compound with an aniline. Examples include, without any limitation, compounds of the general formula $R^8S(O)_2Cl$ (Formula 3) wherein $R^8$ is a carbon-based radical. Examples include, without any limitation, methanesulfonyl chloride, propanesulfonyl chloride, benzenesulfonyl chloride, and p-toluenesulfonyl chloride. Methanesulfonyl chloride is more preferred for reasons of lower cost, ease of addition and/or less waste.

Carbon-based radical refers to a monovalent molecular component comprising a carbon atom that connects the radical to the remainder of the chemical structure through a single bond. Carbon-based radicals can optionally comprise saturated, unsaturated and aromatic groups, chains, rings and ring systems, and heteroatoms. Although carbon-based radicals are not subject to any particular limit in size, in the context of the present disclosure they typically comprise 1 to 16 carbon atoms and 0 to 3 heteroatoms. Of note are carbon-based radicals selected from $C_1$-$C_6$ alkyl, $C_1$-$C_4$ haloalkyl and phenyl optionally substituted with 1-3 substituents selected from $C_1$-$C_3$ alkyl, halogen and nitro.

As used herein, the term "$C_1$-$C_6$ alkyl" includes straight-chain or branched alkyl groups having one to four carbon atoms, e.g., methyl, ethyl, n-propyl, i-propyl, or the different butyl pentyl, or hexyl isomers. As used herein, the term "halogen" includes fluorine, chlorine, bromine and iodine. The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CCl_2$.

As used herein, the term "suitable" indicates that the entity so described is appropriate for use in the situation or circumstance indicated. The term "reacting" and the like refer to adding, contacting, or mixing two or more reagents under appropriate conditions to produce the indicated and/or the desired product. It should be appreciated that the reaction which produces the indicated and/or the desired product may not necessarily result directly from the combination of two reagents which were initially added, i.e. there may be one or more intermediates which are produced in the mixture which ultimately leads to the formation of the indicated and/or the desired product. Reacting can take place in the presence or absence of solvent, at a temperature above room temperature or below room temperature, under an inert atmosphere, etc.

The term "optionally" when used herein means that the optional condition may or may not be present. For example, when a reaction is conducted optionally in the presence of a solvent, the solvent may or may not be present.

The term "optionally substituted" refers to groups which are unsubstituted or have at least one non-hydrogen substituent that does not extinguish the chemical or biological activity possessed by the unsubstituted analog. As used herein, the following definitions shall apply unless otherwise indicated. The term "optionally substituted with" is used interchangeably with the phrase "unsubstituted or substituted with" or with the term "(un)substituted with." Unless otherwise indicated, an optionally substituted group may have a substituent at each substitutable position of the group, and each substitution is independent of the other.

Embodiments of this disclosure include:

Embodiment C1. The composition as described in the Summary comprising (a) a crystalline organic pesticide; (b) a carboxylic acid of Formula 1; (c) an aniline of Formula 2; (d) an amine base; and (e) an aprotic solvent.

Embodiment C2. The composition of Embodiment C1 wherein $R^5$ is Cl.

Embodiment C3. The composition of any one of Embodiments C1 to C2 wherein $R^1$ is $CH_3$.

Embodiment C4. The composition of any one of Embodiments C1 to C3 wherein Z is N.

Embodiment C5. The composition of any one of Embodiments C1 to C4 wherein $R^4$ is Cl, Br or $CF_3$.

Embodiment C6. The composition of any one of Embodiments C1 to C5 wherein $R^2$ is Cl or CN.

Embodiment C7. The composition of any one of Embodiments C1 to C6 wherein $R^4$ is $CH_3$, $R^5$ is Cl, $R^6$ is $CH_3$, $R^1$ is Br, $R^2$ is Cl, $R^3$ is H, and Z is N.

Embodiment C8. The composition of any one of Embodiments C1 to C6 wherein $R^4$ is $CH_3$, $R^5$ is CN, $R^6$ is $CH_3$, $R^1$ is Br, $R^2$ is Cl, $R^3$ is H, and Z is N.

Embodiment C9. The composition of any one of Embodiments C1 to C8 wherein the molar ratio of the compound of Formula 1 to the compound of Formula 2 is from about 1.2:1 to about 1:1.2.

Embodiment C10. The composition of any one of Embodiments C1 to C9 wherein the molar ratio of the compound of Formula 1 to the compound of Formula 2 is from about 1:1 to about 1:1.2.

Embodiment C11. The composition of any one of Embodiments C1 to C10 wherein the molar ratio of the compound of Formula 1 to the compound of Formula 2 is about 1:1.1.

Embodiment C12. The composition of any one of Embodiments C1 to C11 wherein the molar ratio of the sulfonyl chloride to the compound of Formula 1 is at least about 1:1.

Embodiment C13. The composition of any one of Embodiments C1 to C12 wherein the molar ratio of the sulfonyl chloride to the compound of Formula 1 is from about 1:1 to about 2.5:1.

Embodiment C14. The composition of any one of Embodiments C1 to C13 wherein the molar ratio of the sulfonyl chloride to the compound of Formula 1 is from about 1.1:1 to about 1.4:1.

Embodiment C15. The composition of any one of Embodiments C1 to C14 wherein the amount of the amine base is at least about 2 equivalents relative to the sulfonyl chloride of Formula 3.

Embodiment C16. The composition of any one of Embodiments C1 to C15 wherein the amount of amine base is at least about 2.1 equivalents relative to the sulfonyl chloride of Formula 3.

Embodiment C17. The composition of any one of Embodiments C1 to C16 wherein the amount of the amine base is from about 2.1 to 2.2 equivalents relative to the sulfonyl chloride of Formula 3.

Embodiment C18. The composition of any one of Embodiments C1 to C17 wherein the amine base is selected from tertiary amines (including optionally substituted pyridines).

Embodiment C19. The composition of any one of Embodiments C1 to C18 wherein the amine base is selected from optionally substituted pyridines and mixtures thereof.

Embodiment C20. The composition of any one of Embodiments C1 to C19 wherein the amine base is selected from 2-picoline, 3-picoline, 2,6-lutidine, pyridine and mixtures of the foregoing.

Embodiment C21. The composition of any one of Embodiments C1 to C20 wherein the amine base is 3-picoline.

Embodiment C22. The composition of any one of Embodiments C1 to C21 wherein the aprotic solvent is selected from nitriles (e.g., acetonitrile, propionitrile), esters (e.g., methyl acetate, ethyl acetate, butyl acetate), ketones (e.g., acetone, methyl ethyl ketone, methyl butyl ketone, haloalkanes (e.g., dichloromethane, trichloromethane), ethers (e.g., ethyl ether, methyl tert-butyl ether, tetrahydrofuran, p-dioxane), aromatic hydrocarbons (e.g., benzene, toluene, chlorobenzene, dichlorobenzene), tertiary amines (e.g., trialkylamines, dialkylanilines, optionally substituted pyridines), and mixtures of the foregoing.

Embodiment C23. The composition of Embodiment C22 wherein the aprotic solvent is selected from tertiary amines (e.g., trialkylamines, dialkylanilines, optionally substituted pyridines) and mixtures of the foregoing.

Embodiment C24. The composition of Embodiment C22 wherein the solvent is selected from nitriles (e.g., acetonitrile, proprionitrile), esters (e.g., methyl acetate, ethyl acetate, butyl acetate), ketones (e.g., acetone, methyl ethyl ketone, methyl butyl ketone, haloalkanes (e.g., dichloromethane, trichloromethane), ethers (e.g., ethyl ether, methyl tert-butyl ether, tetrahydrofuran, p-dioxane), aromatic hydrocarbons (e.g., benzene, toluene, chlorobenzene, dichlorobenzene), and mixtures of the foregoing.

Embodiment C25. The composition of Embodiment C22 wherein the solvent is acetonitrile.

Embodiment C26. The composition of any one of Embodiments C1 to C25 wherein the molar ratio of the crystalline organic pesticide to the compound of Formula 1 is greater than 0.001:1.

Embodiment C27. The composition of any one of Embodiments C1 to C26 wherein the molar ratio of the crystalline organic pesticide to the compound of Formula 1 is greater than 0.01:1.

Embodiment C28. The composition of any one of Embodiments C1 to C25 wherein the molar ratio of the crystalline organic pesticide to the compound of Formula 1 is between about 0.001:1 and 0.25:1.

Embodiment C29. The composition of any one of Embodiments C1 to C26 wherein the molar ratio of the crystalline organic pesticide to the compound of Formula 1 is between about 0.01:1 and 0.2:1.

Embodiment C30. The composition of any one of Embodiments C1 to C29 wherein the molar ratio of the crystalline organic pesticide to the compound of Formula 1 is between about 0.05:1 and 0.2:1.

Embodiment C31. The composition of any one of Embodiments C1 to C27 wherein the molar ratio of the crystalline organic pesticide to the compound of Formula 1 is greater than 0.09:1.

Embodiment C32. The composition of any one of Embodiments C1 to C31 wherein the molar ratio of the crystalline organic pesticide to the compound of Formula 1 is between about 0.10:1 and 0.25:1.

Embodiment C32a. The composition of any one of Embodiments C1 to C32 wherein the molar ratio of the crystalline organic pesticide to the compound of Formula 1 is between about 0.1:1 and 0.2:1.

Embodiment C33. The composition of any one of Embodiments C1 to C32a wherein the molar ratio of the crystalline organic pesticide to the compound of Formula 1 is about 0.1:1.

Embodiment C34. The composition of any one of Embodiments C1 to C32a wherein the molar ratio of the crystalline organic pesticide to the compound of Formula 1 is about 0.125:1.

Embodiment C34a. The composition of any one of Embodiments C1 to C32a wherein the molar ratio of the crystalline organic pesticide to the compound of Formula 1 is about 0.15:1.

Embodiment C35. The composition of any one of Embodiments C1 to C32a wherein the molar ratio of the crystalline organic pesticide to the compound of Formula 1 is about 0.20:1. Embodiment C36. The composition of any one of Embodiments C1 to C35 wherein the crystalline organic pesticide is a fungicide.

Embodiment C37. The composition of any one of Embodiments C1 to C35 wherein the crystalline organic pesticide is a bactericide.

Embodiment C38. The composition of any one of Embodiments C1 to C35 wherein the crystalline organic pesticide is an herbicide.

Embodiment C39. The composition of any one of Embodiments C1 to C35 wherein the crystalline organic pesticide is a nematocide.

Embodiment C40. The composition of any one of Embodiments C1 to C35 wherein the crystalline organic pesticide is an insecticide.

Embodiment C41. The composition of any one of Embodiments C1 to C35 wherein the crystalline organic pesticide is selected from chlorantraniliprole, cyantraniliprole, flutriafol, indoxacarb, imidacloprid, fluindapyr and combinations thereof.

Embodiment C42. The composition of any one of Embodiments C1 to C35 wherein the organic pesticide is an anthranilic diamide of Formula 4,

4

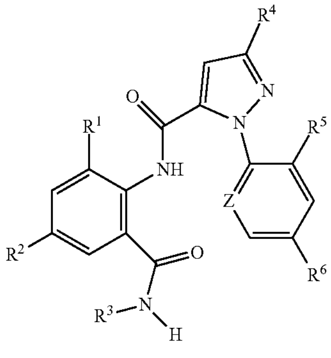

Embodiment C43. The composition of any one of Embodiments C1 to C35 wherein the crystalline organic pesticide is selected from chlorantraniliprole and cyantraniliprole.

Embodiment C44. The composition of any one of Embodiments C1 to C35 wherein the crystalline organic pesticide is chlorantraniliprole.

Embodiment C45. The composition of any one of Embodiments C1 to C35 wherein the crystalline organic pesticide is cyantraniliprole.

Embodiment M1. The method as described in the Summary to prepare a compound of Formula 4-A comprising the steps of: (1) forming the composition of any one of Embodiments C1 to C45; (2) reacting the composition with a sulfonyl chloride compound of Formula 3; and (3) allowing the activated mixture to proceed for the formation of a compound of Formula 4-A.

Embodiment M2. The method of Embodiment M1 wherein the molar ratio of the sulfonyl chloride of Formula 3 to the compound of Formula 1 is at least about 1:1.

Embodiment M3. The method of any one of Embodiments M1 to M2 wherein the molar ratio of the sulfonyl chloride of Formula 3 to the compound of Formula 1 is from about 1:1 to about 2.5:1.

Embodiment M4. The method of any one of Embodiments M1 to M3 wherein the molar ratio of the sulfonyl chloride of Formula 3 to the compound of Formula 1 is from about 1.1:1 to about 1.4:1.

Embodiment M5. The method of any one of Embodiments M1 to M4 wherein when $R^2$ is Br, Cl or I, then the molar ratio of the sulfonyl chloride of Formula 3 to the compound of Formula 1 is about 1.2:1.

Embodiment M6. The method of any one of Embodiments M1 to M4 wherein when $R^2$ is CN, then the molar ratio of the sulfonyl chloride of Formula 3 to the compound of Formula 1 is about 1.3:1.

Embodiment M7. The method of any one of Embodiments M1 to 6 wherein $R^8$ is $C_1$-$C_4$ alkyl, $C_1$-$C_2$ haloalkyl, or phenyl optionally substituted with 1-3 substituents selected from the group consisting of halogen, $C_1$-$C_3$ alkyl and nitro.

Embodiment M8. The method of any one of Embodiments M1 to M7 wherein $R^8$ is $C_1$-$C_2$ alkyl, $CF_3$, phenyl or 4-methylphenyl.

Embodiment M9. The method of any one of Embodiments M1 to M8 wherein $R^8$ is $C_1$-$C_2$ alkyl, phenyl or 4-methylphenyl.

Embodiment M10. The method of any one of Embodiments M1 to M9 wherein $R^8$ is $CH_3$.

Embodiment M11. The method of any one of Embodiments M1 to M10 wherein the temperature of the composition is between about −70 and 100° C. before reacting with the sulfonyl chloride of Formula 3.

Embodiment M12. The method of any one of Embodiments M1 to M11 wherein the temperature of the composition is between about −10 and 50° C.

Embodiment M13. The method of any one of Embodiments M1 to M11 wherein the temperature of the composition is between about 10 and 40° C.

Embodiment M14. The method of Embodiments any one of M1 to M11 wherein the temperature is about 20° C.

Embodiment M15. The method of any one of Embodiments M1 to M14 further comprising the step of: (4) adding water to the reaction.

Embodiment M16. The method of Embodiment M15 wherein the molar ratio of water to the compound of Formula 1 is at least 1:1.

Embodiment M17. The method of Embodiment M15 wherein the molar ratio of water to the compound of Formula 1 is from about 1:1 to about 100:1.

Embodiment M18. The method of Embodiment M15 wherein the molar ratio of water to the compound of Formula 1 is from about 10:1 to about 50:1.

Embodiment M19. The method of Embodiment M15 wherein the molar ratio of water to the compound of Formula 1 is from about 15:1 to about 40:1.

Embodiment M20. The method of Embodiment M15 wherein the molar ratio of water to the compound of Formula 1 is from about 20:1 to about 35:1.

Embodiment M21. The method of any one of Embodiments M15 to M20 wherein the temperature during addition of water is between about −70 and 100° C.

Embodiment M22. The method of any one of Embodiments M15 to M20 wherein the temperature during addition of water position is between about 0 and 80° C.

Embodiment M23. The method of any one of Embodiments M15 to M20 wherein the temperature during addition of water is between about 15 and 75° C.

Embodiment M24. The method of any one of Embodiments M15 to M20 wherein the temperature during addition of water is between about 20 and 65° C.

Embodiment M25. The method of any one of Embodiments M15 to M20 wherein the temperature during addition of water is between about 40 and 60° C.

Embodiment M26. The method of any one of Embodiments M15 to M20 wherein the temperature during addition of water is at least 50° C.

Embodiment M27. The method of any one of Embodiments M15 to M20 wherein the temperature during addition of water is about 65° C.

Embodiment F1. The compound of Formula 4-A is prepared by the method of any one of Embodiments M1 to M27.

Embodiment F2. The composition of Embodiment F1 wherein $R^5$ is Cl.

Embodiment F3. The composition of any one of Embodiments F1 to F2 wherein $R^1$ is $CH_3$.

Embodiment F4. The composition of any one of Embodiments F1 to F3 wherein Z is N.

Embodiment F5. The composition of any one of Embodiments F1 to F4 wherein $R^4$ is Cl, Br or $CF_3$.

Embodiment F6. The composition of any one of Embodiments F1 to F5 wherein $R^2$ is Cl or CN.

Embodiment F7. The composition of any one of Embodiments F1 to F6 wherein $R^4$ is $CH_3$, $R^5$ is Cl, $R^6$ is $CH_3$, $R^1$ is Br, $R^2$ is Cl, $R^3$ is H, and Z is N.

Embodiment F8. The composition of any one of Embodiments F1 to F6 wherein $R^4$ is $CH_3$, $R^5$ is CN, $R^6$ is $CH_3$, $R^1$ is Br, $R^2$ is Cl, $R^3$ is H, and Z is N.

Embodiments C1 through C45; M1 through M27; F1 through F8; and any other Embodiment or Embodiments described herein can be combined in any manner, and the descriptions of variables in the embodiments pertain not only to anthranilic diamides of Formulae 4 and 4-A but also to the starting intermediate compounds of Formulae 1, 2 and 3 useful for preparing the organic pesticides.

Of particular note is that methods of this disclosure prevent formation of highly viscous suspensions prior to reacting with sulfonyl chlorides of Formula 3. One skilled in the art will recognize viscous suspensions impede stirring resulting in reduced control of heat transfer and reagent mixing. One skilled in the art would further recognize reactor capacity and production scale is limited as further solvent addition is necessary to maintain reaction control resulting in increased production costs and waste. A feature of the present method provides an easily stirrable free flowing reaction suspension throughout the process and allows for convenient control of the coupling process as compared to previously known processes for the production of an organic pesticide such as an anthranilic diamide Formula 4-A. In some embodiments the present method provides increased production capacity of an organic pesticide resulting from the benefits of improved stirring, heat transfer and reaction control.

In some embodiments, the crystalline organic pesticide may act as a nucleation source during crystallization of the organic pesticide. In some embodiments, the crystalline organic pesticide may lead to improved solid state characteristics in terms of larger crystals with more uniform crystal size distribution providing significantly reduced filtration times in operating the method on commercial scale and the need for time-consuming cleaning of the reactor from batch to batch.

In various embodiments, wherein up to about 10 mol % of the crystalline organic pesticide is part of the composition in step (1), additional crystalline organic pesticide may be added after the addition of a part of the acid activating agent, such as at least about 5 mol % of the acid activating agent, or about 10 mol % to about 20 mol % of the activating agent, or about 15 mol % to about 20 mol % of the activating agent, in step (2). Alternatively, a reactor that has already produced the crystalline organic pesticide may be used in place of the crystalline organic pesticide, in step (1).

In various embodiments, the methods of the disclosure may be conducted over a wide range of temperatures, but commonly it is conducted at temperatures ranging from −70° C. to 100° C. or from 0° C. to reflux or from 10° C. to 70° C. In some embodiments, the reaction is conducted at a temperature of about 20° C. One skilled in the art would recognize the temperature of the disclosed exothermic reaction is readily controlled by simply controlling the rate of addition of the sulfonyl chloride compound.

The crystalline organic pesticides used in the composition of this disclosure are biologically active compounds or agents including crystalline forms of insecticides, fungicides, nematocides, bactericides, acaricides, herbicides, herbicide safeners, growth regulators such as insect molting inhibitors and rooting stimulants, chemosterilants, semiochemicals, repellents, attractants, pheromones, feeding stimulants and other biologically active compounds or entomopathogenic bacteria, virus or fungi.

Examples of organic pesticides of this disclosure which may be used in the disclosed composition are insecticides such as abamectin, acephate, acequinocyl, acetamiprid, acrinathrin, acynonapyr, afidopyropen ([(3S,4R,4aR,6S,6aS,12R,12aS,12bS)-3-[(cyclopropylcarbonyl)oxy]-1,3,4,4a,5,6,6a,12,12a,12b-decahydro-6,12-dihydroxy-4,6a,12b-trimethyl-11-oxo-9-(3-pyridinyl)-2H,11H-naphtho[2,1-b]pyrano[3,4-e]pyran-4-yl]methyl cyclopropanecarboxylate), amidoflumet, amitraz, avermectin, azadirachtin, azinphos-methyl, benfuracarb, bensultap, benzpyrimoxan, bifenthrin, kappa-bifenthrin, bifenazate, bistrifluron, borate, broflanilide, buprofezin, cadusafos, carbaryl, carbofuran, cartap, carzol, chlorantraniliprole, chlorfenapyr, chlorfluazuron, chloroprallethrin, chlorpyrifos, chlorpyrifos-e, chlorpyrifos-methyl, chromafenozide, clofentezin, chloroprallethrin, clothianidin, cyantraniliprole, (3-bromo-1-(3-chloro-2-pyridinyl)-N-[4-cyano-2-methyl-6-[(methylamino)carbonyl]phenyl]-1H-pyrazole-5-carboxamide), cyclaniliprole (3-bromo-N-[2-bromo-4-chloro-6-[[(1-cyclopropylethyl)amino]carbonyl]phenyl]-1-(3-chloro-2-pyridinyl)-1H-pyrazole-5-carboxamide), cycloprothrin, cycloxaprid ((5S,8R)-1-[(6-chloro-3-pyridinyl)methyl]-2,3,5,6,7,8-hexahydro-9-nitro-5,8-Epoxy-1H-imidazo[1,2-a]azepine), cyenopyrafen, cyflumetofen, cyfluthrin, beta-cyfluthrin, cyhalodiamide, cyhalothrin, gamma-cyhalothrin, lambda-cyhalothrin, cypermethrin, alpha-cypermethrin, zeta-cypermethrin, cyromazine, deltamethrin, diafenthiuron, diazinon, dicloromesotiaz, dieldrin, diflubenzuron, dimefluthrin, dimehypo, dimethoate, dimpropyridaz, dinotefuran, diofenolan, emamectin, emamectin benzoate, endosulfan, esfenvalerate, ethiprole, etofenprox, epsilon-metofluthrin, etoxazole, fenbutatin oxide, fenitrothion, fenothiocarb, fenoxycarb, fenpropathrin, fenvalerate, fipronil, flometoquin (2-ethyl-3,7-dimethyl-6-[4-(trifluoromethoxy)phenoxy]-4-quinolinyl methyl carbonate), flonicamid, fluazaindolizine, flubendiamide, flucythrinate, flufenerim, flufenoxuron, flufenoxystrobin (methyl (αE)-2-[[2-chloro-4-(trifluoromethyl)phenoxy]methyl]-α-(methoxymethylene)benzeneacetate), fluensulfone (5-chloro-2-[(3,4,4-trifluoro-3-buten-1-yl)sulfonyl]thiazole), fluhexafon, fluopyram, flupiprole (1-[2,6-dichloro-4-(trifluoromethyl)phenyl]-5-[(2-methyl-2-propen-1-yl)amino]-4-[(trifluoromethyl)sulfinyl]-1H-pyrazole-3-carbonitrile), flupyradifurone (4-[[(6-chloro-3-pyridinyl)methyl](2,2-difluoroethyl)amino]-2(5H)-furanone), flupyrimin, fluvalinate, tau-fluvalinate, fluxametamide, fonophos, formetanate, fosthiazate, gamma-cyhalothrin, halofenozide, heptafluthrin ([2,3,5,6-tetrafluoro-4-(methoxymethyl)phenyl]methyl 2,2-dimethyl-3-[(1Z)-3,3,3-trifluoro-1-propen-1-yl]cyclopropanecarboxylate), hexaflumuron, hexythiazox, hydramethylnon, imidacloprid, indoxacarb, insecticidal soaps, isofenphos, isocycloseram, kappa-tefluthrin, lambda-cyhalothrin, lufenuron, malathion, meperfluthrin ([2,3,5,6-tetrafluoro-4-(methoxymethyl)phenyl]methyl (1R,3S)-3-(2,2-dichloroethenyl)-2,2-dimethylcyclopropanecarboxylate), metaflumizone, metaldehyde, methamidophos, methidathion, methiocarb, methomyl, methoprene, methoxychlor, metofluthrin, methoxyfenozide, epsilon-metofluthrin, epsilon-momfluorothrin, monocrotophos, monofluorothrin ([2,3,5,6-tetrafluoro-4-(methoxymethyl)phenyl]methyl 3-(2-cyano-1-propen-1-yl)-2,2-dimethylcyclopropanecarboxylate), nicotine, nitenpyram, nithiazine, novaluron, noviflumuron, oxamyl, oxazosulfyl, parathion, parathion-methyl, permethrin, phorate, phosalone, phosmet, phosphamidon, pirimicarb, profenofos, profluthrin, propargite, protrifenbute, pyflubumide (1,3,5-trimethyl-N-(2-methyl-1-oxopropyl)-N-[3-(2-methylpropyl)-4-[2,2,2-trifluoro-1-methoxy-1-(trifluoromethyl)ethyl]phenyl]-1H-pyrazole-4-carboxamide), pymetrozine, pyrafluprole, pyrethrin, pyridaben, pyridalyl, pyrifluquinazon, pyriminostrobin (methyl (αE)-2-[[[2-[(2,4-dichlorophenyl)amino]-6-(trifluoromethyl)-4-pyrimidinyl]oxy]methyl]-α-(methoxymethylene)benzeneacetate), pyriprole, pyriproxyfen, rotenone, ryanodine, silafluofen, spinetoram, spinosad, spirodiclofen, spiromesifen, spiropidion, spirotetramat, sulprofos, sulfoxaflor (N-[methyloxido[1-[6-(trifluoromethyl)-3-pyridinyl]ethyl]-$\lambda^4$-sulfanylidene]cyanamide), tebufenozide, tebufenpyrad, teflubenzuron, tefluthrin, kappa-tefluthrin, terbufos, tetrachlorantraniliprole, tetrachlorvinphos, tetramethrin, tetramethylfluthrin ([2,3,5,6-tetrafluoro-4-(methoxymethyl)phenyl]methyl 2,2,3,3-tetramethylcyclopropanecarboxylate), tetraniliprole, thiacloprid, thiamethoxam, thiodicarb, thiosultap-sodium, tioxazafen (3-phenyl-5-(2-thienyl)-1,2,4-oxadiazole), tolfenpyrad, tralomethrin, triazamate, trichlorfon, triflumezopyrim (2,4-dioxo-1-(5-pyrimidinylmethyl)-3-[3-(trifluoromethyl)phenyl]-2H-pyrido[1,2-a]pyrimidinium inner salt), triflumuron, tyclopyrazoflor, zeta-cypermethrin, *Bacillus thuringiensis* delta-endotoxins, entomopathogenic bacteria, entomopathogenic viruses or entomopathogenic fungi.

Further examples of organic pesticides of this disclosure which may be used in the disclosed composition are: fungicides such as acibenzolar-S-methyl, aldimorph, ametoctradin, aminopyrifen, amisulbrom, anilazine, azaconazole, azoxystrobin, benalaxyl (including benalaxyl-M), benodanil, benomyl, benthiavalicarb (including benthiavalicarb-isopropyl), benzovindiflupyr, bethoxazin, binapacryl, biphenyl, bitertanol, bixafen, blasticidin-S, boscalid, bromuconazole, bupirimate, buthiobate, carboxin, carpropamid, captafol, captan, carbendazim, chloroneb, chlorothalonil, chlozolinate, copper hydroxide, copper oxychloride, copper sulfate, coumoxystrobin, cyazofamid, cyflufenamid, cymoxanil, cyproconazole, cyprodinil, dichlobentiazox, dichlofluanid, diclocymet, diclomezine, dicloran, diethofencarb, difenoconazole, diflumetorim, dimethirimol, dimethomorph, dimoxystrobin, diniconazole (including diniconazole-M), dinocap, dipymetitrone, dithianon, dithiolanes, dodemorph, dodine, econazole, etaconazole, edifenphos, enoxastrobin (also known as enestroburin), epoxiconazole, ethaboxam, ethirimol, etridiazole, famoxadone, fenamidone, fenaminstrobin, fenarimol, fenbuconazole, fenfuram, fenhexamide, fenoxanil, fenpiclonil, fenpicoxamid, fenpropidin, fenpropimorph, fenpyrazamine, fentin acetate, fentin hydroxide, ferbam, ferimzone, flometoquin, florylpicoxamid, fluopimomide, fluazinam, fludioxonil, flufenoxystrobin, fluindapyr, flumorph, fluopicolide, fluopyram, fluoxapiprolin, fluoxastrobin, fluquinconazole, flusilazole, flusulfamide, flutianil, flutolanil, flutriafol, fluxapyroxad, folpet, fthalide (also known as phthalide), fuberidazole, furalaxyl, furametpyr, hexaconazole, hymexazole, guazatine, imazalil, imibenconazole, iminoctadine albesilate, iminoctadine triacetate, inpyrfluxam, iodicarb, ipconazole, ipfentrifluconazole, ipflufenoquin, isofetamid, iprobenfos, iprodione, iprovalicarb, isoflucypram, isoprothiolane, isopyrazam, isotianil, kasugamycin, kresoxim-methyl, lancotrione, mancozeb, mandipropamid, mandestrobin, maneb, mapanipyrin, mefentrifluconazole, mepronil, meptyldinocap, metalaxyl (including metalaxyl-M/mefenoxam), metconazole, methasulfocarb, metiram, metominostrobin, metyltetraprole, metrafenone, myclobutanil, naftitine, neo-asozin (ferric methanearsonate), nuarimol, octhilinone, ofurace, orysastrobin, oxadixyl, oxathiapiprolin, oxolinic acid, oxpoconazole, oxycarboxin, oxytetracycline, penconazole, pencycuron, penflufen, penthiopyrad, perfurazoate, phosphorous acid (including salts thereof, e.g., fosetyl-aluminm), picoxystrobin, piperalin, polyoxin, probenazole, prochloraz, procymidone, propamocarb, propiconazole, propineb, proquinazid, prothiocarb, prothioconazole, pydiflumetofen (Adepidyn®), pyraclostrobin, pyrametostrobin, pyrapropoyne, pyraoxystrobin, pyraziflumid, pyrazophos, pyribencarb, pyributacarb, pyridachlometyl, pyrifenox, pyriofenone, perisoxazole, pyrimethanil, pyrifenox, pyrrolnitrin, pyroquilon, quinconazole, quinmethionate, quinofumelin, quinoxyfen, quintozene, silthiofam, sedaxane, simeconazole, spiroxamine, streptomycin, sulfur, tebuconazole, tebufloquin, teclofthalam, tecloftalam, tecnazene, terbinafine, tetraconazole, thiabendazole, thifluzamide, thiophanate, thiophanate-methyl, thiram, tiadinil, tolclofos-methyl, tolprocarb, tolyfluanid, triadimefon, triadimenol, triarimol, triazoxide, tribasic copper sulfate, triclopyricarb, tridemorph, trifloxystrobin, triflumizole, trimoprhamide tricyclazole, trifloxystrobin, triforine, triticonazole, uniconazole, validamycin, valifenalate (also known as valifenal), vinclozolin, zineb, ziram, zoxamide and 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone; nematocides such as fluopyram, spirotetramat, thiodicarb, fosthiazate, abamectin, iprodione, fluensulfone, dimethyl disulfide, tioxazafen, 1,3-dichloropropene (1,3-D), metam (sodium and potassium), dazomet, chloropicrin, fenamiphos, ethoprophos, cadusaphos, terbufos, imicyafos, oxamyl, carbofuran, tioxazafen, *Bacillus firmus* and *Pasteuria nishizawae*; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad.

General references for organic pesticides (i.e. insecticides, fungicides, nematocides, acaricides, herbicides and biological agents) include *The Pesticide Manual,* 13*th Edition*, C. D. S. Tomlin, Ed., British Crop Protection Council, Farnham, Surrey, U. K., 2003 and *The BioPesticide Manual, 2nd Edition*, L. G. Copping, Ed., British Crop Protection Council, Farnham, Surrey, U. K., 2001.

In some embodiments a material with a similar crystal structure or similar crystal structure characteristics as the compounds of Formula 4-A may be used as a heterogeneous nucleation source to form and grow desired product crystals. Materials with crystal structures similar to the compounds of Formula 4-A may also be used to induce beneficial polymorphic characteristics that result in improved chemical reaction processes.

An organic pesticide of Formula 4-A is formed when the starting compounds of Formulae 1, 2 and 3 are contacted with each other in a combined liquid phase, in which each is at least partially soluble. Particularly as the starting materials of Formulae 1 and 2 are typically solids at ordinary ambient temperatures, the method is most satisfactorily conducted using a solvent in which the starting compounds have significant solubility. Thus typically the method is conducted in a liquid phase comprising a solvent. In some cases the carboxylic acid of Formula 1 may have only slight solubility but its salt with added base may have more solubility in the solvent. Suitable solvents for this method include nitriles such as acetonitrile and propionitrile; esters such as methyl acetate, ethyl acetate, and butyl acetate; ketones such as acetone, methyl ethyl ketone (MEK), and methyl butyl ketone; haloalkanes such as dichloromethane and trichloromethane; ethers such as ethyl ether, methyl tert-butyl ether, tetrahydrofuran (THF), and p-dioxane; aromatic hydrocarbons such as benzene, toluene, chlorobenzene, and dichlorobenzene; tertiary amines such as trialkylamines, dialkylanilines, and optionally substituted pyridines; and mixtures of the foregoing. Solvents of note include acetonitrile, proprionitrile, ethyl acetate, acetone, MEK, dichloromethane, methyl tert-butyl ether, THF, p-dioxane, toluene, and chlorobenzene. Of particular note as solvent is acetonitrile, as it often provides products in superior yield and/or purity.

As the reaction of the present method generates hydrogen chloride as a byproduct, which would otherwise bind to basic centers on the compounds of Formulae 1, 2 and 4, the method is most satisfactorily conducted in the presence of at least one added base. The base can also facilitate constructive interaction of the carboxylic acid with the sulfonyl chloride compound and the anthranilamide. Reaction of an added base with the carboxylic acid of Formula 1 forms a salt, which may have greater solubility than the carboxylic acid in the reaction medium. Although the base may be added at the same time, in alternation, or even after the addition of the sulfonyl chloride, the base is typically added before the addition of the sulfonyl chloride. Some solvents such as tertiary amines also serve as bases, and when these are used as solvents they will be in large stoichiometric excess as bases. When the base is not used as solvent the nominal mole ratio of the base charged to the sulfonyl chloride charged is typically from about 2.0 to 2.2, and is preferably from about 2.1 to 2.2. Preferred bases are tertiary amines, including substituted pyridines. More preferred bases include 2-picoline, 3-picoline, 2,6-lutidine, and pyridine. Of particular note as base is 3-picoline, as its salts with carboxylic acids of Formula 1 are often highly soluble in solvents such as acetonitrile.

Typically more than one solid form can exist in the production of anthranilic diamides of Formulae 4 and 4-A. Thus, an anthranilic diamide of Formulae 4 and 4-A include all crystalline and non-crystalline forms of anthranilic diamides within the genus represented by Formulae 4 and 4-A. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability.

One skilled in the art will appreciate that a polymorph of anthranilic diamides of Formulae 4 and 4-A can exhibit beneficial effects (e.g., suitability for improved stirring, heat transfer and filtration) relative to another polymorph or a mixture of polymorphs of the same anthranilic diamide of Formulae 4 and 4-A. Preparation and isolation of a particular polymorph of anthranilic diamides of Formulae 4 and 4-A can be achieved by methods known to those skilled in the art including, for example, crystallization using selected solvents and temperatures. For a comprehensive discussion of polymorphism see R. Hilfiker, Ed., *Polymorphism in the Pharmaceutical Industry*, Wiley-VCH, Weinheim, 2006.

Without further elaboration, it is believed that one skilled in the art using the preceding description can utilize the present disclosure to its fullest extent. The following examples are, therefore, to be construed as merely illustrative, and not limiting of the disclosure in any way whatsoever. Steps in the following examples illustrate a procedure for each step in an overall synthetic transformation, and the starting material for each step may not have necessarily been prepared by a particular preparative run whose procedure is described in other examples or steps. Ambient or room temperature is defined as about 20-25° C. Percentages are by weight except where otherwise indicated. All patents and publications cited herein are fully incorporated by reference in their entirety.

Example 1

Preparation of 3-bromo-1-(3-chloro-2-pyridinyl)-N-[4-cyano-2-methyl-6-[(methylamino)-carbonyl]phenyl]-1H-pyrazole-5-carboxamide (cyantraniliprole)

To a mixture of crystalline 3-bromo-1-(3-chloro-2-pyridinyl)-N-[4-cyano-2-methyl-6-[(methylamino)carbonyl]phenyl]-1H-pyrazole-5-carboxamide (10.3 g, 0.020 mol), 3-bromo-1-(3-chloro-2-pyridinyl)-1H-pyrazole-5-carboxylic acid (see PCT Patent Publication WO 03/015519 for preparation) (40.0 g, 0.132 mol) and 2-amino-5-cyano-N,3-dimethylbenzamide (see PCT Patent Publication WO 03/015519 for preparation) (27.5 g, 0.142 mol) was added acetonitrile (123.5 g, 3.01 mol) and stirred at 20° C. 3-picoline (34.5 g, 0.367 mol) was added over 5 min. Methanesulfonyl chloride (19.6 g, 0.171 mol) was added linearly over 1.5 h. The mixture was stirred for 2 h. Water (76.2 g, 4.23 mol) was added linearly over 1.2 h. The pH was adjusted to 1.1 with concentrated hydrochloric acid (4.37 g, 0.043 mol) and the mixture was stirred for 1 h. The pH was then adjusted to 3.3 with sodium hydroxide (4.34 g, 0.027 mol) and the mixture was stirred for 15 min. The mixture was filtered, and the resultant material was washed with aqueous acetonitrile (84% w/w, 43.0 g), then with acetonitrile (83.2 g), and dried to afford the title compound.

Isolated Yield: 95% (seed corrected, based on 3-bromo-1-(3-chloro-2-pyridinyl)-1H-pyrazole-5-carboxylic acid)

Crystal Size Distribution: D[4,3] values were in the range of 50-65 μm containing a small amounts of fines Example 2

Preparation of 3-bromo-1-(3-chloro-2-pyridinyl)-N-[4-cyano-2-methyl-6-[(methyl-amino)carbonyl]phenyl]-1H-pyrazole-5-carboxamide (cyantraniliprole)

Cyantraniliprole was prepared, as in Example 1, in Experiments 1-10 and A-F using the parameters in Tables A, B and C below. Experiments 1-10 were conducted on a scale of 100 g of 3-bromo-1-(3-chloro-2-pyridinyl)-1H-pyrazole-5-carboxylic acid. Experiments A-F were conducted on a scale of 40 g of 3-bromo-1-(3-chloro-2-pyridinyl)-1H-pyrazole-5-carboxylic acid. Experiments A-F were conducted using a 5 cm diameter Büchner Funnel fitted with a Grade GF/B binder free glass fiber filter for filtration and washing the resultant material.

The observations in Tables A and B were made after the addition of 3-picoline and prior to the addition of methanesulfonyl chloride. In Experiments 1-4 the stirring rate to obtain sufficient mixing was measured after the reaction mass thickened.

As can be observed in Tables A and B, the addition of the crystalline organic pesticide to the reagents resulted in improved reaction suspension characteristics. The improved characteristics lead to lower rates of stirring necessary for sufficient reaction mixing. The improved characteristics also lead to agitation with lower solvent usage (i.e. higher reaction concentration).

As can be observed in Table C, as less solvent is used, increased amounts of crystalline organic pesticide is required to control crystallization. The degree of crystallization control is illustrated by the correlation between larger D10 values and improved solid state qualities (i.e. faster filtration and washing times). D1 values indicate the particle size, wherein 10% of the sample contains particles that size or smaller. D50 values indicate the particle size, wherein 50% of the sample contains particles that size or smaller. D90 values indicate the particle size, wherein 90% of the sample contains particles that size or smaller.

The abbreviation "Exp." stands for "Experiment". The abbreviation "rpm." stands for revolutions per minute.

TABLE A

| Description | Exp 1 | Exp 2 | Exp 3 | Exp 4 | Exp 5 |
|---|---|---|---|---|---|
| Crystalline Organic Pesticide Amount (mol %) | 0 | 0 | 0 | 0 | 10 |
| Solvent Usage (mL/mol) | 1800 | 1600 | 1400 | 1200 | 1200 |
| Observed Reaction Suspension Characteristics at 300 rpm | Thick Slurry Formation; Not Stirrable after 20 min. | Thick Slurry Formation; Not Stirrable after 20 min. | Thick Slurry Formation; Not Stirrable after 20 min. | Thick Slurry Formation; Not Stirrable after 20 min. | Good Agitation for 3 h. |
| Stirring Rate to Obtain Sufficient Mixing (rpm) | 800 | 1000 | 1000 | 1000 | 300 |

TABLE B

| Description | Exp 6 | Exp 7 | Exp 8 | Exp 9 | Exp 10 |
|---|---|---|---|---|---|
| Crystalline Organic Pesticide Amount (mol %) | 15 | 10 | 15 | 10 | 15 |
| Solvent Usage (mL/mol) | 1200 | 1000 | 1000 | 600 | 600 |
| Observed Reaction Suspension Characteristics at 300-350 rpm | Good Agitation for 3 h. | Good Agitation for 3 h. | Good Agitation for 3 h. | Good Agitation for 3 h. | Good Agitation for 3 h. |
| Stirring Rate to Obtain Sufficient Mixing (rpm) | 300 | 300 | 300 | 300-350 | 300 |

TABLE C

| Description | Exp A | Exp B | Exp C | Exp D | Exp E | Exp F |
|---|---|---|---|---|---|---|
| Crystalline Organic Pesticide Amount (mol %) | 5 | 10 | 15 | 5 | 10 | 15 |
| Solvent Usage (mL/mol) | 1200 | 1200 | 1200 | 1000 | 1000 | 1000 |
| Filtration time (s) | 150 | 60 | 60 | 150 | 140 | 50 |
| Aqueous acetonitrile wash time (s) | 100 | 20 | 45 | 100 | 100 | 30 |
| Acetonitrile wash time (s) | 100 | 40 | 25 | 100 | 110 | 50 |

TABLE C-continued

| Description | Exp A | Exp B | Exp C | Exp D | Exp E | Exp F |
|---|---|---|---|---|---|---|
| CSD D[4,3] (μm) | 85.5 | 82.7 | 86.1 | 58.2 | 52.0 | 78.5 |
| D10 (μm) | 5.4 | 18.3 | 17.8 | 3.8 | 4.5 | 14.6 |
| D50 (μm) | 34.9 | 82.7 | 50.8 | 21.8 | 27.9 | 47.1 |
| D90 (μm) | 236.9 | 192.8 | 219.0 | 153.9 | 132.5 | 202.6 |

Example 3

Preparation of 3-bromo-1-(3-chloro-2-pyridinyl)-N-[4-cyano-2-methyl-6-[(methylamino)-carbonyl]phenyl]-1H-pyrazole-5-carboxamide (cyantraniliprole)

Crystalline 3-bromo-1-(3-chloro-2-pyridinyl)-N-[4-cyano-2-methyl-6-[(methylamino)-carbonyl]phenyl]-1H-pyrazole-5-carboxamide (22.8 g, 0.043 mol), 3-bromo-1-(3-chloro-2-pyridinyl)-1H-pyrazole-5-carboxylic acid (see PCT Patent Publication WO 03/015519 for preparation) (65.0 g, 0.214 mol), 2-amino-5-cyano-N,3-dimethylbenzamide (see PCT Patent Publication WO 03/015519 for preparation) (42.7 g, 0.221 mol) and acetonitrile (85.0 g, 2.07 mol) were charged into a 400 mL temperature controlled jacketed reactor equipped with a thermometer, an anchor-type mechanical stirrer, syringe pump and a reflux condenser. The mixture was agitated at 250 rpm, and the temperature was adjusted to 20° C. 3-picoline (56.1 g, 0.596 mol) was added over 5 min. Methanesulfonyl chloride (31.8 g, 0.278 mol) was charged into the syringe and added linearly to the reaction mixture over 4.0 h. After the addition of methanesulfonyl chloride was complete, the reaction mixture was heated linearly to 50° C. over 2 h. Water (128.3 g, 7.12 mol) was added over 146.5 min according to the following dosing profile.

| Time (min) | Total Water Added (g) |
|---|---|
| 0 | 0 |
| 14.4 | 2.14 |
| 27.2 | 4.28 |
| 38.5 | 6.42 |
| 48.6 | 8.56 |
| 57.6 | 10.7 |
| 91.4 | 21.4 |
| 112.0 | 32.1 |
| 124.7 | 42.8 |
| 132.8 | 53.5 |
| 138.0 | 64.2 |
| 141.3 | 74.9 |
| 143.4 | 85.6 |
| 144.8 | 96.3 |
| 145.6 | 107 |
| 146.5 | 128.3 |

After the addition of water was complete, the reaction mixture was cooled linearly to 20° C. over 30 min. The mixture was filtered, and the resultant material was washed with aqueous acetonitrile (84% w/w, 140.0 g), then with acetonitrile (135.0 g), and dried to afford the title compound.

Isolated Yield: 95% (seed corrected, based on 3-bromo-1-(3-chloro-2-pyridinyl)-1H-pyrazole-5-carboxylic acid)

Crystal Size Distribution: D[4,3] values were in the range of 50-65 μm containing a small amounts of fines

What is claimed is:

1. A composition comprising:

(a) a crystalline organic pesticide, wherein the crystalline organic pesticide is a crystalline compound of Formula 4,

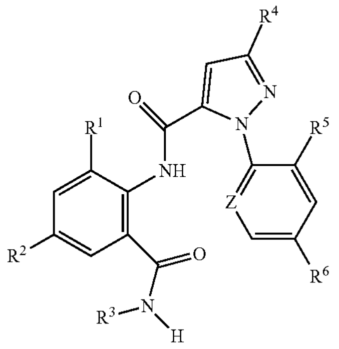

4 wherein $R^1$ is $CH_3$;

$R^2$ is CN;

$R^3$ is $CH_3$;

$R^4$ is Br;

$R^5$ is Cl;

$R^6$ is H; and

Z is N;

(b) a carboxylic acid compound of Formula 1,

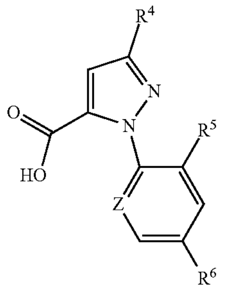

1 wherein $R^4$ is Br;

$R^5$ is Cl;

$R^6$ is H; and

Z is N;

(c) an aniline compound of Formula 2,

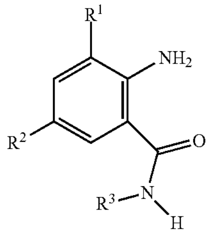

2 wherein $R^1$ is $CH_3$;

$R^2$ is CN;

$R^3$ is $CH_3$;

(d) an amine base and (e) an aprotic solvent, wherein the amount of crystalline compound of Formula 4 is 5 mol % to 30 mol % per mol of the carboxylic acid compound of Formula 1.

2. The composition of claim 1 wherein the amine base is selected from optionally substituted pyridines.

3. The composition of claim 1 wherein the amine base is 3-picoline.

4. The composition of claim 1 wherein the aprotic solvent is acetonitrile.

5. The composition of claim 1 wherein the amount of crystalline compound of Formula 4 is 10 mol % to 25 mol % per mol of the carboxylic acid compound of Formula 1.

6. The method to prepare a compound of Formula 4-A,

4-A

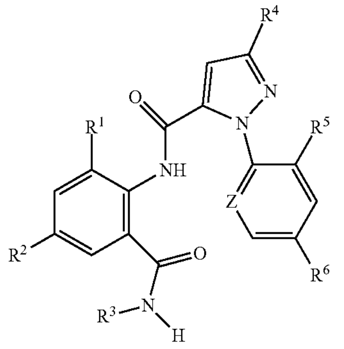

wherein $R^1$ is $CH_3$;

$R^2$ is CN;

$R^3$ is $CH_3$;

$R^4$ is Br;

$R^5$ is Cl;

$R^6$ is H; and

Z is N;

the method comprising the steps of:

(1) forming the composition of claim 1;

(2) reacting the composition of claim 1 with a sulfonyl chloride compound of Formula 3, $$R^8S(O)_2Cl \quad 3$$

wherein $R^8$ is carbon-based radical; and (3) allowing the coupling of the acid activated mixture to proceed for the formation of a compound of Formula 4-A.

7. The method of claim 6 wherein the sulfonyl chloride compound of Formula 3 is methanesulfonyl chloride.

8. The method of claim 6 further comprising the step of:

(4) adding water to the reaction.

9. The composition of claim 1 wherein the amount of the aprotic solvent is at least 600 mL aprotic solvent per mol of the carboxylic acid compound of Formula 1.

10. The composition of claim 1 wherein the amount of the aprotic solvent is between 1800 to 600 mL aprotic solvent per mol of the carboxylic acid compound of Formula 1.

11. The composition of claim 1 wherein the amount of the aprotic solvent is between 1200 to 600 mL aprotic solvent per mol of the carboxylic acid compound of Formula 1.

* * * * *